10

(12) United States Patent
Stegmann et al.

(10) Patent No.: US 7,618,641 B2
(45) Date of Patent: Nov. 17, 2009

(54) FUNCTIONALLY RECONSTITUTED VIRAL MEMBRANES CONTAINING ADJUVANT

(75) Inventors: Antonius Johannes Hendrikus Stegmann, Katwijk (NL); Jan Christiaan Wilschut, Garnwerd (NL); Johannes Henricus Gerardus Van Berkum, Laren (NL)

(73) Assignee: Bestewil Holding B.V., Amsterdam (NL)

( * ) Notice: Subject to any disclaimer, the term of this patent is extended or adjusted under 35 U.S.C. 154(b) by 339 days.

(21) Appl. No.: 10/560,594

(22) PCT Filed: Jun. 18, 2004

(86) PCT No.: PCT/NL2004/000437

§ 371 (c)(1),
(2), (4) Date: Dec. 13, 2005

(87) PCT Pub. No.: WO2004/110486

PCT Pub. Date: Dec. 23, 2004

(65) Prior Publication Data

US 2006/0193873 A1    Aug. 31, 2006

(30) Foreign Application Priority Data

Jun. 19, 2003    (WO) .................... PCT/NL03/00450

(51) Int. Cl.
*A61K 51/00*      (2006.01)
*A61K 39/38*      (2006.01)
*A61K 39/385*     (2006.01)
*A61K 39/12*      (2006.01)
*A61K 39/145*     (2006.01)
*A01N 25/26*      (2006.01)
*A61K 39/205*     (2006.01)

(52) U.S. Cl. .............. 424/204.1; 424/184.1; 424/193.1; 424/196.11; 424/209.1; 424/1.21; 424/417; 977/907

(58) Field of Classification Search ........................ None
See application file for complete search history.

(56) References Cited

U.S. PATENT DOCUMENTS

| 4,542,212 | A |   | 9/1985  | Fauve         |         |
|-----------|---|---|---------|---------------|---------|
| 5,565,203 | A |   | 10/1996 | Glück et al.  |         |
| 5,879,685 | A |   | 3/1999  | Glück et al.  |         |
| 5,936,076 | A |   | 8/1999  | Higa et al.   |         |
| 6,417,326 | B1| * | 7/2002  | Cullis et al. | 530/324 |
| 2001/0053368 | A1 | | 12/2001 | Burt et al.  |         |
| 2003/0092145 | A1 | * | 5/2003 | Jira et al. | 435/173.3 |
| 2003/0113347 | A1 |   | 6/2003 | Cusi et al. |         |
| 2005/0214359 | A1 | * | 9/2005 | Stegmann ................... 424/450 |

FOREIGN PATENT DOCUMENTS

| EP | 0109942    | 10/1983 |
| EP | 0180564    | 10/1985 |
| EP | 0205098    | 6/1986  |
| EP | 0231039    | 1/1987  |
| EP | 0487909    | 10/1991 |
| WO | 88/08718   | 11/1988 |
| WO | WO 92/19267| 11/1992 |
| WO | 02/09746   | 2/2002  |

OTHER PUBLICATIONS

Gluck and Metcalfe, Novel approaches in the development of immunopotentiating reconstituted influenza virosomes as efficient antigen carrier systems, 2003, Vaccine, vol. 21, pp. 611-615.*
Zurbriggen et al., IRIV-adjuvanted hepatitis A vaccine: in vivo absorption and biophysical characterization, 2000, Progress in Lipid Research, vol. 39, pp. 3-18.*
Dijkstra et al., Activation of Murine Lymphocytes by Lipopolysaccharide Incorporated in Fusogenic, Reconstituted Influenza Virus Envelopes (Virosomes), 1996, Journal of Immunology, vol. 157, pp. 1028-1036.*
Bron R et al: "Preparation, Properties, and Applications of Reconstituted Influenza Virus Envelopes (Virosomes)" Methods in Enzymology, Academic Press Inc, San Diego, CA, US, vol. 220, 1993, pp. 313-331, XP002915998 ISSN: 0076-6879 p. 330.
Campagnon B et al: "Targeting of Poly (RL)-Poly (RC) by Fusogenic (F Protein) Immunoliposomes" Experimental Cell Research, San Diego, CA, US, vol. 200, No. 2, Jun. 1992, pp. 333-338, XP008005854 ISSN: 0014-4827 p. 334.
Mengiardi B et al: "Virosomes as carriers for combined vaccines" Vaccine, Butterworth Scientific. Guildford, GB, vol. 13, No. 14, Oct. 1, 1995, pp. 1306-1315, XP004057432 ISSN: 0264-410X the whole document.
Fernandes Isabelle et al: "Synthetic lipopeptides incorporated in liposomes: In vitro stimulation of the proliferation of murine splenocytes and in vivo induction of an immune response against a peptide antigen" Molecular Immunology, vol. 34, No. 8-9, Jun. 1997, pp. 569-576, XP002267110 ISSN: 0161-5890 the whole document.
Stegmann T et al: "Functional Reconstitution of Influenza Virus Envelopes" Embo Journal, Oxford University Press, Surrey, GB, vol. 6, No. 9, 1987, pp. 2651-2660, XP009020387 ISSN: 0261-4189 the whole document.

* cited by examiner

*Primary Examiner*—Gary B Nickol
*Assistant Examiner*—Benjamin P Blumel
(74) *Attorney, Agent, or Firm*—Young & Thompson (57) ABSTRACT

Vaccines directed against antigens such as membrane proteins from pathogens or tumor cells are disclosed. Also described are methods of forming reconstituted viral membranes, with membrane fusion activity, which are lipid bilayer membranes preferably containing natural lipids of a virus, a viral fusion protein, one or more optional further antigens as well as amphiphilic adjuvants. Pharmaceutical compositions including such reconstituted viral membranes are also described.

17 Claims, 7 Drawing Sheets

FUNCTIONALLY RECONSTITUTED VIRAL MEMBRANES CONTAINING ADJUVANT

FIELD OF THE INVENTION

The invention relates to vaccines directed against antigens such as membrane proteins from pathogens or tumor cells. The invention further relates to methods of forming reconstituted viral membranes, with membrane fusion activity, which are lipid bilayer membranes containing the natural lipids of a virus, amphiphilic antigens as well as amphiphilic adjuvants, and to pharmaceutical compositions comprising such reconstituted viral membranes.

BACKGROUND OF THE INVENTION

Classically, vaccines against enveloped viruses either contain killed or live attenuated viruses, or they comprise a preparation of their constituents (e.g. split virus or subunit preparations). For vaccination, these preparations are usually injected. After injection, the viruses or proteins present in such vaccines are taken up by antigen-presenting cells of the immune system such as dendritic cells or macrophages, followed by a presentation of the antigenic parts of the vaccines to effector cells of the immune system. Vaccines are effective when injected because antigen-presenting cells are most abundant just under the skin. However, it has now become clear that similar cells are also present in the mucosa that, for instance, lines the nose (Ogra et al. 2001). In order to induce these phagocytes present in the mucosa to mount an immune response, much stronger stimulation is required than for those present under the skin (Janeway et al. 2001).

While the injection of some viruses or proteins contained in vaccines, for example influenza or measles virus, elicits an immune response that is sufficiently strong to protect against a later infection by the same virus, this is not the case for many others, for example respiratory syncytial virus. Numerous attempts to reinforce the immune response by physical or chemical means have been undertaken. The most important principles that have emerged from such experiments are: (1) for physical stimulation, multiple copies of the viral proteins need to be combined in particles. These particles can be whole viruses, reconstituted viral membranes, or proteins on microparticle carriers. Particles stimulate the immune system better than individual subunits (Ogra et al. 2001; Janeway et al. 2001). (2) Chemical stimulation on the other hand requires that the phagocytes or the effector cells of the immune system receive certain signals through receptors present on surface of the antigen-presenting cell, for instance through the use of adjuvants, chemical compounds that are recognized by these receptors.

With sufficient additional physicochemical stimulation, viral proteins can elicit strong immune responses even if applied to mucous membranes, for example upon application to the nose (Ogra et al. 2001). Most of the current methods and compositions for stimulating an immune response by such means, whether by chemical or physical means or combinations of the two principles, have significant disadvantages that will be outlined below.

A particular kind of vaccine composition that was developed in the art is known as 'virosomes', which are lipid bilayers containing viral glycoproteins. Virosomes may comprise reconstituted viral membranes, generally produced by extraction of membrane proteins and lipids from enveloped viruses with a detergent, followed by addition of lipids, and removal of said detergent from the extracted viral membrane proteins and lipids, such that characteristic lipid bilayers are formed with the proteins protruding from them (Stegmann et al. 1987). Virosomes may also comprise membranes formed from purified viral proteins and synthetic or natural lipids, or other substances that will form a bilayer. A characteristic feature of virosomes is that they closely mimic the composition, surface architecture and functional activities of the native viral envelope. A particularly important characteristic of said virosomes involves the preservation of the receptor-binding and membrane fusion activity of the native viral envelope, allowing the virosomes to enter the same cells that the virus would be able to enter, and to be presented to the immune system by these same cells. Preservation of receptor-binding and membrane fusion activity is essential for expression of the full immunogenic properties of said virosomes (Arkema 2000; Bungener 2002).

For some viral antigens, virosomes elicit protective immune responses that can be strong even when the vaccine is, for example, delivered intranasally (as is exemplified in WO 88/08718 and WO 92/19267). However, other virosome formulations exhibit only marginally improved immunogenicity as compared to killed virus or subunit preparations (as exemplified in (Glück et al. 1994). In this cited example, the virosomes were generated through a protocol involving addition of exogenous lipids, which we have found to result in a composition of the virosomes and a surface architecture different from those in the native viral envelope. It is known to a person skilled in the art that such a different surface architecture may affect the membrane fusion properties of the virosomes produced and thus their immunogenicity.

To enhance the immune response, allowing intranasal application of this vaccine, an adjuvant protein from *Escherichia coli* (heat-labile toxin) was mixed with the lipid-supplemented virosome influenza vaccine (EP 0 538 437). Clinical trials indicated that addition of the toxin was absolutely required to induce serum antibody titers equivalent to injected vaccine (Glück et al. 1994). Although addition of the toxin did thus enhance the immunogenicity of this vaccine, it also induced a serious side effect known as Bell's Palsy, a temporary paralysis of facial muscles. Since the adjuvating effect of the toxin is due to recognition by an antigen-presenting cell, there is no certainty in this case that the toxin and the viral protein will contact the same cell, and therefore a relatively high concentration of the toxin will be needed in order to ensure activation of every cell, increasing the chance that antigens will be recognized by an activated cell. Therefore this type of virosome preparation with added lipids has a fair number of disadvantages.

Virosomes have also been prepared from purified influenza antigens, mixed with derivatives of muramyldipeptide (EP 0 205 098 and EP 0 487 909). In this case, the muramyldipeptide derivative forms the membrane. Although muramyldipeptide is an adjuvant, and the formulation was indeed found to enhance the immune response to the influenza antigens, muramyl dipeptides are pyrogenic (Kotani et al., 1976; Dinarello et al., 1978), are cleared rapidly from the body following injection, and have local toxicity leading to granulomas and inflammation (Ribi et al., 1979; Kohashi et al., 1980). Moreover, they have a limited shelf life at neutral pH (Powell et al., 1988), and the optimal pH to maintain their structural integrity is too low to allow their formulation in a vaccine together with the fusion protein of viruses that enter cells by receptor-mediated endocytosis, such as the hemagglutinin of influenza virus. Moreover, such synthetic membranes are not a good mimic of the natural viral membrane and thus the immune response to them will differ from that generated against the virus.

Alternatively, researchers in the art have also generated complexed antigens different from reconstituted viral membranes, such as 'Immunostimulatory Complexes' (ISCOMs, Morein et al. 1984), containing viral proteins complexed with adjuvants such as saponins like Quil A® (EP 0231039B1; EP 0109942A1; EP 0180564A1), most of which are isolated from the bark of *Quillaia sopanaria Molina*. Mixed with antigen, and lipids such as cholesterol, these adjuvants form cage-like structures of between 30-40 nm, rendering the antigen particulate, while acting at the same time as an adjuvant. Although ISCOMs have been used in a number of veterinary vaccines, and enhance the immunogenicity of the viral membrane proteins, the development of such vaccines for humans has been inhibited by concerns about their toxicity and the complexity of the mixture (Cox et al. 1998).

More recently, proteosome influenza vaccines were developed (US application 20010053368), consisting of non-covalent complexes of the purified outer membrane proteins of bacteria such as meningococci, mixed with antigenic proteins such as the influenza hemagglutinin or the human immunodeficiency envelope glycoprotein. While these multiple bacterial proteins may act as adjuvants, the complex nature of such mixtures, consisting of multiple proteins, will present a regulatory issue. Moreover, the immune response is directed against all of the proteins and other antigens present in the solution, and less specifically against the viral proteins.

Another particulate formulation developed by Biovector Therapeutics consists of an inner core of carbohydrate surrounded by a lipid envelope containing antigens. With influenza hemagglutinin as the antigen, some enhancement of the immune response was noted, but not significant enough to warrant further development.

Live attenuated versions of respiratory viruses, such as a cold-adapted strain of influenza virus with minimal replication in the respiratory tract have been developed as intranasal vaccines. These vaccines have the distinct advantage of inducing immune responses that are close to the natural immunity induced by an infection with wild-type virus. For influenza, such vaccines have been known since the 1980's, and now appear close to commercialization. The delay has been caused by the ability, that many viruses share, to mutate rapidly, causing the attenuated viruses to revert partially of wholly to wild-type virus, and thereby in fact causing the disease they were meant to prevent.

For the above reasons, it is well recognized in the art that, especially to induce immune responses for pathogens that do not by themselves induce a strong immune response, and for intranasal and other mucosal applications, although compositions such as ISCOM's and proteosomes were developed, there still is a great need for well characterized vaccine compositions that induce a strong immune response, do not contain live virus, and have a low toxicity.

SUMMARY OF THE INVENTION

The present invention provides novel means and methods that solve a number of problems and difficulties outlined above. The invention provides a reconstituted viral membrane comprising an amphiphilic adjuvant and an antigen, wherein said adjuvant and said antigen interact through hydrophobic interactions, are both present with the lipid bilayer membrane of the reconstituted viral membranes, and in which the reconstituted viral membrane has membrane fusion activity that is superior to that of virosomes prepared according to EP 0 538 437. The reconstituted viral membrane further closely mimics the composition, surface architecture and functional properties of the viral envelope from which the reconstituted viral membrane is derived. The invention further provides a method for producing such reconstituted viral membranes, comprising some or all of the following steps: i) dissolving the virus in a suitable detergent ii) removing the viral genetic material and core proteins iii) contacting one or more amphiphilic molecules having adjuvant activity and an antigen in a solution comprising a detergent; and iv) removing the detergent under conditions that allow reformation of the membrane.

Moreover, the invention provides a pharmaceutical preparation comprising reconstituted viral membranes according to the invention, a pharmaceutically acceptable carrier, as well as the use of such reconstituted viral membranes or a pharmaceutical preparation according to the invention in therapy or prophylaxis, either by intranasal, oral or parenteral delivery.

DESCRIPTION OF THE INVENTION

In a first aspect, the present invention pertains to a reconstituted viral membrane. The reconstituted viral membrane preferably comprises: (a) a lipid bilayer; (b) a fusion protein of a virus; (c) an amphiphilic adjuvant; and, (d) optionally, a further antigen. In the reconstituted viral membrane, preferably, the lipid bilayer has a lipid composition that is compatible with fusion, as induced by the fusion protein, of the viral membrane with a host cell of a natural host of the virus. Preferably lipid composition is compatible with fusion at the optimal pH of fusion. Preferably, the fusion protein, the amphiphilic adjuvant and preferably also the optional further antigen interact with the hydrophobic interior of the lipid bilayer, i.e. are associated with, integrated into, and/or embedded in the bilayer of the viral membrane through hydrophobic interactions with the lipids of the bilayer and/or each other. Further preferred is that the fusion protein and the amphiphilic adjuvant are not covalently linked. Preferably, the amphiphilic adjuvant and the further antigen are also not covalently linked. The viral membranes of the invention are preferably functionally reconstituted viral membranes comprising lipids, preferably natural lipids of a virus, an amphiphilic adjuvant, a viral fusion protein and one or more antigens, wherein the amphiphilic adjuvant, lipids viral fusion proteins and antigens interact primarily through hydrophobic interactions, wherein the hydrophobic part of the amphiphilic adjuvant preferably forms an integral part of a lipid bilayer membrane, which bilayer further contains the fusion protein, antigen(s) and lipids. By functional reconstitution is meant, that the reconstituted membrane has membrane fusion activity. A preferred reconstituted viral membrane is in the form of a vesicle.

A fusion protein of a virus of a virus is herein understood to mean an integral membrane protein of a virus, usually an enveloped virus that, if expressed on the surface of a suitable mammalian (or avian) cell, can induce fusion of the cell, at an appropriate pH, with cells that are a natural host for the virus (see e.g. Hernandez et al., 1996). Examples of viral fusion proteins for incorporation into the reconstituted viral membrane include the Semliki Forest virus E1 protein, the Influenza virus hemagglutinin (HA) protein, the HIV gp120/gp41 proteins, the F proteins of paramyxoviruses. Two types of viral fusion protein induced fusion can be distinguished. The first type of fusion, such as e.g. induced by the HIV gp120/gp41 proteins, occurs at neutral pH at the surface of the targeted host cell. The second type of fusion, such as e.g. induced by the Influenza virus hemagglutinin (HA) protein, occurs upon internalization at lower pH (5.0-6.5) from within the endosomal compartment of the host cell. Both types of fusion are specifically included in the present invention.

The capability of the reconstituted viral membranes of the invention to fuse with a host cell is thus dependent on the presence of an appropriate viral fusion protein. However, this capability is further dependent of the lipid composition of the bilayer of the reconstituted viral membrane, as virosomes composed of synthetic lipids and viral fusion proteins have been described in the art that are incapable of fusion. The lipid composition of the reconstituted viral membranes is thus preferably chosen such that the membranes are capable of fusion with appropriate host cells at an appropriate pH. The capability of the reconstituted viral membranes to fuse may be assayed in an erythrocyte ghost fusion assay as e.g. described in Example 3 herein. For reconstituted viral membranes comprising the influenza hemagglutinin, a preferred fusion activity in this assay induces the fusion of at least 30% of reconstituted viral membrane vesicles with erythrocyte ghosts after 1 minute, if 1 µM virosomes is mixed with 50 µM erythrocyte ghosts membrane phospholipid at a pH that is optimal for the hemagglutinin in question.

A preferred fusion activity for other reconstituted viral membranes, that cannot be tested by the above assay, is the fusion upon addition of the reconstituted viral membranes to cells capable of being infected by the virus from which their fusion proteins are derived. The reconstituted membranes should fuse at least 10% of the cells that would be fused by the virus from which their fusion proteins are derived.

One preferred lipid composition that provides the reconstituted viral membranes with fusion activity is a lipid composition that comprises natural lipids of a virus. The term "natural lipids of a virus" is herein understood to mean those lipids that are present in the membrane of a virus grown on cells, preferably mammalian, or grown on embryonated eggs. The natural lipids of a virus are thus preferably obtained or isolated from virus particles thus grown, as opposed to synthetic lipids. However, functionally reconstituted viral membranes of the invention may comprise purified lipids from other sources, e.g. synthetic lipids, in addition to the natural lipids. A lipid composition for the provision of the reconstituted viral membranes with fusion activity is thus preferably a composition that is obtained or obtainable from natural viral membranes. Lipid compositions for use in the present invention thus include compositions exclusively composed of natural lipids of a virus, compositions composed of natural lipids of a virus supplemented with lipids from other sources, as well as compositions composed of lipids from various sources, which mimic the lipid composition of a natural viral membrane.

Adjuvants are herein intended to include any substance or compound that, when used, in combination with an antigen, to immunise a human or an animal, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a mammal, thereby excluding immunostimulatory compounds that are endogenous to mammals, such as e.g. interleukins, interferons and other hormones. The adjuvants to be incorporated in the functionally reconstituted viral membranes of the invention are preferably amphiphilic adjuvants.

The term "amphiphilic adjuvant" is intended to include any adjuvant, including compounds like lipopeptides and glycolipids, having hydrophobic membrane embedded and environment oriented polar (head group) moieties and which, preferably by itself, can associate with, or more preferably integrate into lipid bilayer vesicles or micelles in water. The term also includes any amphiphilic adjuvant that is stably incorporated into lipid bilayers (comprising the natural lipids of a virus) with its hydrophobic moiety in contact with the interior, hydrophobic region of the bilayer membrane, and its polar head group moiety oriented toward the exterior, polar surface of the membrane. However, more hydrophobic adjuvants having a less pronounced amphiphilicity, i.e. having no or only weakly polar head group moieties, but which can associate with, or integrate into lipid bilayer vesicles, are specifically not excluded from the invention. The "amphiphilic adjuvants" with adjuvant activity as used herein, thus include naturally occurring or (partly) synthetic adjuvants that are capable of forming a reconstituted viral membrane together with one or more antigens of interest and natural lipids of a virus in an aqueous environment under conditions that allow the formation of a reconstituted viral membrane.

In a preferred embodiment, the amphiphilic adjuvant present in the reconstituted viral membrane is pharmaceutically acceptable for use in humans, in contrast to e.g. Quil A™ or other saponins, which are amphiphiles with adjuvant activity that have been tested in certain settings in the art. The amphiphilic adjuvants of the invention are preferably not covalently linked to the antigens but are present together in the lipid bilayer of the reconstituted membrane. The fact the antigen and adjuvant are not covalently linked assures that processing of the antigen and presentation of its epitopes to the immune system is essentially identical to that of the natural protein alone, ensuring good recognition of the protein present on the natural pathogen. On the other hand, the hydrophobic interaction of the antigen and the adjuvant with the lipid bilayer (and each other) allows for a distribution of the adjuvant and antigen over the reconstituted viral membranes in a preparation whereby the majority of the membrane vesicles in a preparation contain both the antigen and adjuvant in a single vesicle, more preferably at least 60, 70, 80, 90, 95 or 95% of the vesicles contain both the antigen and adjuvant. The combination of antigen and adjuvant in a single membrane or vesicle allows delivery of the antigen to the antigen presenting cell that is activated by the adjuvant, thereby increasing the therapeutic and/or prophylactic efficacy of the reconstituted viral membranes.

In a preferred embodiment of the invention said amphiphilic adjuvant is recognized by a Toll-like-receptor (TLR) present on antigen presenting cells. Various compounds recognized by TLR's are known in the art and include e.g. lipopeptides, lipopolysaccharides, peptidoglycans, liopteichoic acids, lipoproteins (from mycoplasma, mycobacteria or spirochetes), double-stranded RNA (poly I:C), unmethylated DNA, lipoarabinomannan, flagellin, CpG-containing DNA, and imidazoquinolines. Not all TLR-recognised compounds are suitable as adjuvants as e.g. the toxicity of wild-type Gram-negative bacterial lipopolysaccharides is too high for them to be used as adjuvants, i.e. they are not pharmaceutically acceptable for use in humans. The other TLR-recognised compounds may however be used as adjuvants. Such TLR-recognized adjuvants may be amphiphilic adjuvants by themselves, or alternatively they may be modified into an amphiphilic adjuvant, e.g. by coupling hydrophobic compounds (see below) to a polar TLR ligand. Alternatively, the amphiphilic adjuvants may target other receptors. A preferred amphiphilic adjuvant is a lipopeptide, which may be produced synthetically or semi-synthetically. A preferred lipopeptide for use as amphiphilic adjuvant has adjuvant activity and is pharmaceutically acceptable for use in humans. A lipopeptide of the invention is a molecule that will usually consist of one or more (oligo)peptides covalently coupled to one or more hydrophobic compounds selected from fatty acids, lipids, ceramides, plasmalogens, alkyl or alkene chains, or sterols. Generally, lipopeptides for use in the present invention preferably comprise 3, 4, 5, 6, 7, or 8, amino acids, preferably the peptides comprise 40-70% amino acids that are positively charged, of which lysine and arginine are preferred, and preferably the peptides comprises one or more serines and/or cysteines. Especially preferred lipopeptides are listed in Table 1.

In another embodiment of the invention said amphiphilic adjuvant is a glycolipid. A preferred glycolipid for use as amphiphilic adjuvant has adjuvant activity and is pharmaceutically acceptable for use in humans. Glycolipids are lipids (or other hydrophobic compounds) covalently coupled to one or more sugars. In a highly preferred embodiment the invention provides reconstituted viral membranes according to the invention, in which the glycolipid is a α-galactosylceramide or a phosphatidyl inositol mannoside. The terms "an α-galactosylceramide" and "a phosphatidyl inositol mannoside" are intended to include any derivative of either one. Derivatives of these molecules having adjuvant activity and that are useful in the context of the present invention are e.g. described in U.S. Pat. No. 5,936,076 and in U.S. Pat. No. 4,542,212, respectively. Other suitable glycolipid adjuvants for use in the invention include e.g. modified forms of endotoxic lipopolysaccharides (LPS) of Gram-negative bacteria having reduced toxicity of the Lipid A portion the LPS but retaining (part of) the adjuvant activity, as may be obtained from genetically modified Gram negative pathogens and as reviewed in WO02/09746.

A modified LPS for use as amphiphilic adjuvant in the invention preferably has a modified Lipid A moiety with reduced toxicity. The toxicity of a modified LPS preferably is less than the toxicity of a corresponding wild-type LPS, more preferably the toxicity of the modified LPS is less than 90, 80, 60, 40, 20, 10, 5, 2, 1, 0.5 or 0.2% of the toxicity of the wild-type LPS. The toxicities of wild-type and various modified LPS's with reduced toxicity may be determined in any suitable assay known in the art. A preferred assay for determining the toxicity, i.e. the biological activity of the modified LPS's is the WEHI test for TNF-alpha induction in the MM6 macrophage cell line (Espevik and Niessen, 1986, J. Immunol. Methods 95: 99-105; Ziegler-Heitbrock et al., 1988, Int. J. Cancer 41: 456-461). On the other hand, a modified LPS with reduced toxicity should still have sufficient immunostimulatory activity, i.e. adjuvant activity. The modified LPS with reduced toxicity preferably has at least 10, 20, 40, 80, 90 or 100% of the immunostimulatory activity of the corresponding wild-type LPS. The immunostimulatory activity may be determined in vivo in laboratory animals as described above or in the Examples herein, or in vitro, e.g. determining the maturation of dendritic cells stimulated by incubation with the LPS to be tested by measuring the production of at least one cytokine (e.g. one of IL12, IL10, INF-alpha, IL6 and IL-1-beta) by the LPS-stimulated dendritic cells, or by measuring the expression of at least one costimulatory molecule (e.g. CD40 or CD86) on the LPS-stimulated dendritic cells.

In another aspect of the present invention, the amphiphilic adjuvant present in the virosome according to the invention, is a peptide, preferably an amphiphilic peptide. A preferred peptide for use as amphiphilic adjuvant has adjuvant activity and is pharmaceutically acceptable for use in humans. Peptides, in particular polar peptides, with adjuvant activity may be rendered into amphiphilic adjuvants by (covalently) linking them to a suitable hydrophobic compound (see above). Alternatively, amphiphilic peptides may comprise a hydrophobic stretch of amino acids such as a transmembrane sequence as described below. A preferred peptide comprises a sequence from the Notch ligand Jagged-1 (see Weijzen et al., 2002; Genbank accession no. AAC 52020) or a sequence from the Staphylococcus aureus protein A. Peptides having sequences from Jagged-1 or protein A are preferably covalently coupled to a suitable hydrophobic compound (see above) and/or comprise a transmembrane sequence (see below). The (polar) part of the Jagged-1 or protein A derived peptides that protrudes from the lipid bilayer preferably comprises no more than 3, 4, 5, 6, 7, or 8, amino acids.

The reconstituted viral membranes of the invention are preferably suitable for both parenteral and mucosal (e.g. intranasal or oral) administration. An important aspect of the present invention is, however, that the reconstituted viral membranes of the present invention can be applied for intranasal delivery of antigens that would not normally elicit a sufficient immune response upon intranasal delivery in the treated subject to protect against subsequent infection by the pathogenic organism comprising the antigen.

The reconstituted viral membranes of the invention comprise a viral fusion protein and, optionally a further antigen. Thus, it is to be understood that the reconstituted viral membranes comprising only a viral fusion protein and no further antigens are a part of the invention, in which case the viral fusion protein also has a function as antigen, in addition to its function as fusion protein. On the other hand, the reconstituted viral membranes may thus comprise one or more further antigens in addition to the viral fusion protein.

The antigens that are part of the reconstituted viral membrane according to the invention preferably have a hydrophobic part that is capable of being inserted in the lipid bilayer membrane of the reconstituted viral membrane vesicle. Many pathogenic entities such as viruses, bacteria, yeasts and parasites carry in their capsid, cell wall or membrane, proteins that elicit an immune response in the host. Examples of antigens that have hydrophobic elements, such as e.g. transmembrane segments, and that are suited to be part of a reconstituted viral membrane according to the invention are proteins present in the membrane (also called envelope in the case of viruses) of the pathogen. Therefore, in preferably, the antigen present in the reconstituted viral membrane of the invention is an integral membrane protein. The antigenic proteins in the reconstituted viral membranes of the present invention are oriented in the same way as they appear on the viral or cellular membrane, but may present epitopes that are normally partially or at least temporarily hidden when present in a membrane lipid bilayer. Stimulation of the immune system by these antigen-presenting reconstituted viral membranes may be due to a combination of their specific recognition by cells of the immune system, their particular character, the presentation of the protein, and the uncovering of hidden epitopes. Preferably, the antigenic proteins that are used in the reconstituted viral membranes of the invention comprise one or more protective epitopes, i.e. epitopes capable of eliciting an immune response in a mammal that provides protection against infection by the pathogen from which the antigen is derived, or that provides protection against a tumor expressing the antigen.

In preferred embodiments, said antigens are derived from a virus, a parasite, a fungus or a bacterium. Especially preferred are reconstituted viral membranes, wherein said antigen is derived from influenza virus. Proteins from influenza virus that can be used in reconstituted viral membranes of the present invention are preferably the hemagglutinin (HA) protein, the neuramidase (NA) protein and/or the M2 protein, alone or in combination.

Antigens that can be applied and used in the formation of the reconstituted viral membranes according to the invention can be derived from all sorts of viruses, non-limiting examples of such viruses are: Retroviridae such as Human Immunodeficiency virus (HIV); a rubellavirus; paramyxoviridae such as parainfluenza viruses, measles, mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxyiridae such as smallpox virus, and African swine fever virus. Likewise such antigens may be derived from pathogenic bacteria, fungi (including yeasts), or parasites. Such antigens include bacterial antigens of e.g. *Helicobacter*, such as *H. pylori*, *Neisseria*, such as *N. mengitidis*, *Haemophilus*, such as *H. influenza*, *Bordetella*, such as *B. pertussis*, *Chlamydia*, *Streptococcus*, such as *Streptococcus* sp. serotype A, *Vibrio*, such as *V. cholera*, Gram-negative enteric pathogens including e.g. *Salmonella*, *Shigella*, *Campylobacter* and *Escherichia*, as well as antigen from bacteria causing anthrax, leprosy, tuberculosis, diphtheria, Lyme disease, syphilis, typhoid fever, and gonorrhea. Antigens from parasites e.g. include antigens from protozoans, such as *Babeosis bovis*, *Plasmodium*, *Leishmania* spp. *Toxoplasma gondii*, and *Trypanosoma*, such as *T. cruzi*. Fungal antigens may include antigens from fungi such as *Aspergillus* sp., *Candida albicans*, *Cryptococcus*, such as e.g *C. neoformans*, and *Histoplasma capsulatum*.

Although vaccination is generally applied for the prophylactic protection against pathogens or for the treatment of diseases following pathogenic infection, the person skilled in the art is aware of the application of vaccines for tumor-treatment. Moreover, an increasing number of tumor-specific proteins are found to be proper entities that can be targeted by human or humanized antibodies. Such tumor-specific proteins are also within the scope of the present invention. Many tumor specific antigens are known in the art. Therefore, in one preferred embodiment, the present invention provides reconstituted viral membranes comprising a tumor-specific antigen. Suitable tumor antigens include e.g. carcinoembryonic antigen, prostate-specific membrane antigen, prostate specific antigen, protein MZ2-E, polymorphic epithelial mucin (PEM), folate-binding-protein LK26, truncated epidermal growth factor receptor (EGRF), Thomsen-Friedenreich (T) antigen, GM-2 and GD-2 gangliosides, Ep-CAM, mucin-1, epithialial glycoprotein-2, and colon specific antigen.

Preferred antigens from these pathogens are integral membrane proteins. However, non-membrane protein antigens or parts thereof containing protective epitopes may also be modified for use in the present invention fusing them to a transmembrane sequence. Transmembrane sequences or membrane-anchoring sequences are well known in the art and are based on the genetic geometry of mammalian transmembrane molecules. A transmembrane sequence usually consists of a stretch of about 10-30, usually around 20 amino acids, the majority of which having hydrophobic side chains. Transmembrane sequences are known for a wide variety of proteins and any of these may be used. Examples of membrane-anchoring sequences for use in the present invention include e.g. those derived from CD8, ICAM-2, IL-8R, CD4 and LFA-1. Preferably a transmembrane sequence is derived from viral integral membrane protein that is naturally present in a viral membrane. Examples thereof include the transmembrane region of human respiratory syncytial virus (RSV) glycoprotein G (e.g. amino acids 38 to 63) or the transmembrane region of influenza virus neuraminidase (e.g. amino acids 7 to 27).

In another aspect, the present invention provides a method for producing a reconstituted viral membrane, comprising some or all of the following steps: (a) mixing an amphiphilic adjuvant, a viral fusion protein, an optional further antigen, and lipids in a solution comprising a detergent; (b) decreasing the concentration of the detergent under conditions that allow reconstitution of a viral membrane comprising a lipid bilayer in which the amphiphilic adjuvant and the viral fusion protein interact with the hydrophobic interior of the lipid bilayer, whereby preferably the amphiphilic adjuvant and the viral fusion protein are not covalently linked, whereby preferably also the amphiphilic adjuvant and the optional further antigen are not covalently linked, and whereby the reconstituted viral membrane has membrane fusion activity; (c) optionally, purifying the reconstituted viral membrane; and, (d) optionally, formulating the reconstituted viral membrane into a pharmaceutical composition. For the provision of viral lipids the method may further comprise: i) dissolving the virus in a suitable detergent such as octaethyleneglycol mono-N-dodecylether ii) removing the viral genetic material and core proteins e.g. by differential ultracentrifugation The detergent concentration is preferably decreased by dialysis, diafiltration or absorption onto hydrophobic (and/or into size exclusion) beads, at the appropriate rate of removal of the detergent, that allows reformation of the membrane, wherein preferably the amphiphilic adjuvant and the viral fusion protein and preferably also the further antigen, present in said reconstituted viral membrane, interact through hydrophobic interactions, with the interior, hydrophobic region of the bilayer membrane, and/or with each other. The virus preferably is a membrane-containing virus such as most enveloped viruses. Preferred viruses for use as source of natural viral lipids are influenza viruses, Semliki Forest virus, or paramyxoviruses.

Preferably, the method for producing a reconstituted viral membrane disclosed by the present invention comprises the step of purifying said reconstituted viral membrane. Methods for purification of reconstituted viral membranes are known in the art and include e.g. differential and density gradient centrifugation and/or chromatography (size exclusion-, ion exchange- and/or affinity-chromatography). Detergents are amphiphilic molecules with surface activity Suitable detergents are detergent that efficiently dissolve the viral membrane components, but that do not denature the fusion protein, viral capsid and/or core proteins, e.g. zwitterionic detergents such as octaethyleneglycol mono-N-dodecylether.

Hydrophobic interactions result from non-covalent, non-electrostatic attraction forces between hydrophobic substances that are present in an aqueous environment. In a further aspect the present invention provides a pharmaceutical preparation comprising as active ingredient a reconstituted viral membrane according to the invention, and a pharmaceutically acceptable carrier. Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the reconstituted viral membranes to the patient. Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment. Pharmaceutically acceptable carriers for parenteral delivery are exemplified by sterile buffered 0.9% NaCl or 5% glucose optionally supplemented with a 20% albumin. Preparations for parental administration must be sterile. The parental route for administration of the polypeptide or antibody is in accord with known methods, e.g. injection or infusion by intravenous, intraperitoneal, intramuscular, intrarterial or intralesional routes. The reconstituted viral membranes are preferably administered by bolus injection. A typical pharmaceutical composition for intramuscular injection would be made up to contain, for example, 1-10 ml of phosphate buffered saline and 1 to 100 μg, preferably 15-45 μg (of antigen protein) of the reconstituted viral membranes of the present invention. For oral administration, the active ingredient can be administered in liquid dosage forms, such as elixirs, syrups, and suspensions. Liquid dosage forms for oral administration can contain coloring and flavoring to increase patient acceptance. Methods for preparing parenterally, orally or intranasally administrable compositions are well known in the art and described in more detail in various sources, including, for example, Remington's Pharmaceutical Science (15th ed., Mack Publishing, Easton, Pa., 1980) (incorporated by reference in its entirety for all purposes). In a further aspect, the invention relates to a method for vaccination against, or for prophylaxis or therapy of an infectious disease or tumor by administration of a therapeutically or prophylactically effective amount of (a pharmaceutical composition comprising) reconstituted viral membranes of the invention to a subject in need of prophylaxis or therapy. The invention also relates to reconstituted viral membranes of the invention for use as a medicament, preferably a medicament for vaccination against, or for prophylaxis or therapy of an infectious disease or tumor. The invention further relates to the use of reconstituted viral membranes of the invention in the manufacture of a medicament for vaccination against, or for prophylaxis or therapy of an infectious disease or tumor.

EXAMPLES

Example 1

Production of a Reconstituted Viral Membrane Containing the Lipopeptide N-palmitoyl-S-2,3(bispalmitoyloxy)-propyl-cysteinyl-seryl-(lysil)$_3$-lysine, the Natural Lipids of Influenza Virus and the Influenza Membrane Proteins Influenza virus was produced by growing virus acquired from the World Influenza Center or the American Type Tissue Culture Collection (ATCC), using methods known to persons skilled in the art, for instance by growing the virus on embryonated eggs or cultured cells. The virus was then purified, preferably by differential or density gradient ultracentrifugation or a combination thereof, and may subsequently be inactivated by beta-propiolactone or formaldehyde according to established standard procedures.

The purified and concentrated influenza A/Panama/2007/9 virus (1500 nmol phospholipid) was incubated with 1 ml of the detergent octa(thylene glycol)-n-dodecyl monoether (C12E8) (Boehringer, Mannheim, Germany) at a concentration of 100 mM (a concentration above the detergent's critical micelle concentration is required), for 10 min at 4° C., in an isotonic buffer at neutral pH: 145 mM NaCl, 2.5 mM HEPES, 1 mm EDTA, pH 7.4 (Buffer A). The viral nucleocapsid and matrix proteins were then removed by centrifugation at 100,000×g for 30 min at 4° C. The pellet was discarded, and the supernatant mixed with the dry lipopeptide at a ratio of 0.5 mg lipopeptide per 750 nmol of viral lipid, and mixed until the lipopeptide was dissolved. 128 mg of BioBeads SM-2 (Bio-Rad) were then added to each 350 microliters of the mixture, and the detergent was removed by shaking the mixture and the beads vigorously for one hour. The fluid was then transferred to another 64 mg of these beads and shaking was continued for 10 minutes. The resulting turbid supernatant contains the reconstituted viral membranes, and can be used for vaccination with or without further purification.

Figure 1:
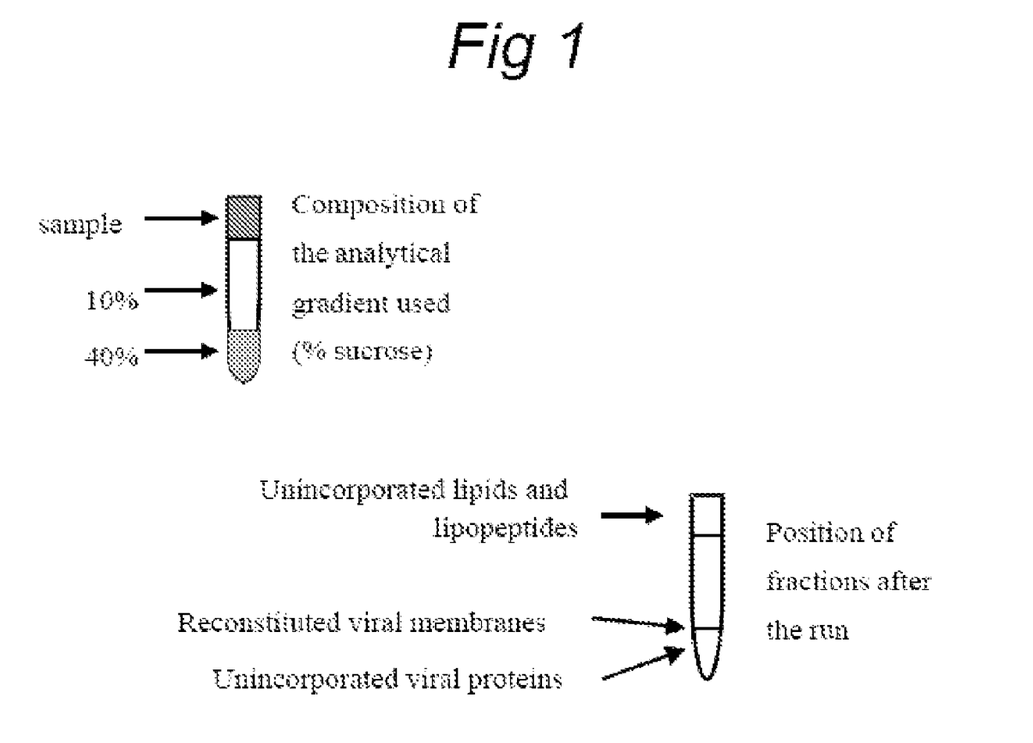
FIG. 1: Schematic drawing of the sucrose gradient used to analyze the physical association between lipopeptides, protein and lipids of the adjuvant-containing reconstituted viral membranes.

For analysis of the physical association between the lipids, lipopeptides and viral proteins, the turbid mixture containing the reconstituted viral membranes was loaded atop a discontinuous sucrose gradient, containing a 1 mL cushion of 40% sucrose (w/v) in buffer A and a 4 mL top layer of 10% sucrose (w/v) in buffer A (as depicted in FIG. 1). The gradients were centrifuged for 90 minutes at 100.000 $g_{max}$, and samples were taken from the 40% cushion, the interface between the 40% cushion and 10% top layer, and from the top. In these gradients, unincorporated viral proteins move into the cushion during centrifugation, lipid and lipopeptides not present in the reconstituted membranes move to the top of the gradient, and reconstituted viral membranes can be found at the interface (FIG. 1). 15% of the viral lipid was found near the top of the gradient, as was 6% of the lipopeptide. 85% of the viral lipid, 94% of the lipopeptide, and 60% of the viral membrane protein loaded on the gradient were found to be associated with the reconstituted viral membrane band.

Figure 2:
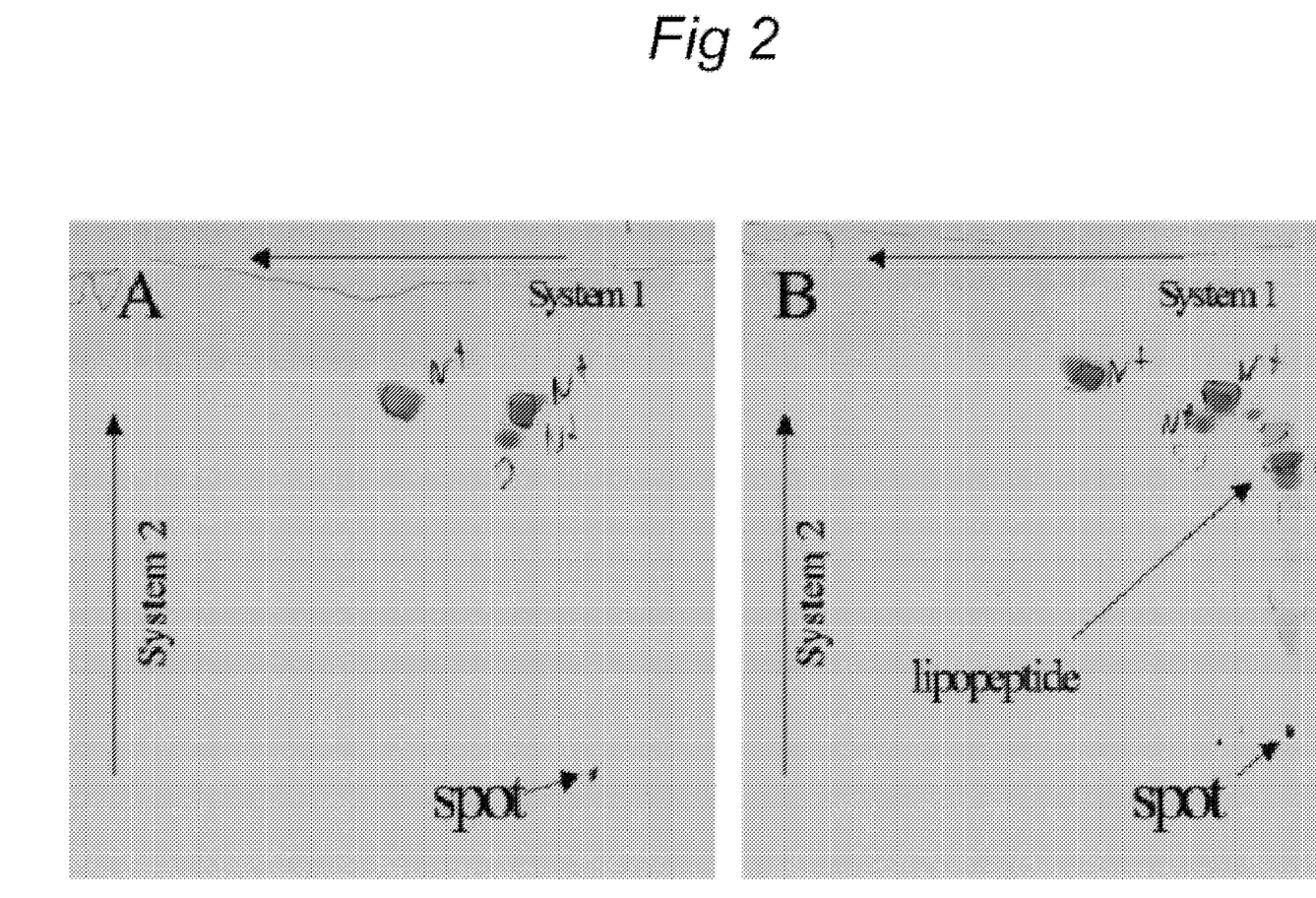
FIG. 2: Two-dimensional thin layer chromatogram of the lipids and lipopeptides recovered from the 10/40% sucrose interface on gradients as outlined in FIG. 1. Panel A: control, reconstituted viral membranes without lipopeptide, showing the ninhydrin-reactive natural viral lipids. Panel B: reconstituted viral membranes containing lipopeptides, showing the natural viral lipids reactive with ninhydrin, and the ninhydrin-reactive lipopeptides in addition. The chromatograms were developed in two dimensions: system 1 $CHCl_3$/methanol/$H_2O$ 65/25/4, system 2 N-butanol/acetic acid/water 2/1/1, and stained by derivatization with ninhydrin stain. Sample loading sites are marked "spot".

To analyze the lipid composition of the band, two samples of reconstituted viral membranes, prepared according to the above protocol, or in the absence of added lipopeptide, were recovered from the 40/10% interface of sucrose gradient as described above, and extracted with CHCL3/MeoH, according to Folch et al. (1957). The extracted lipids and lipopeptides were analyzed by two-dimensional thin layer chromatography, with CHCl₃/methanol/H₂O 65/25/4 as the first eluent, followed by N-butanollacetic acid/water 2/1/1, and stained by derivatization with ninhydrin stain (the plate was sprayed with 2% ninhydrin in N-butanol, and incubated at 80° C. for 10 minutes). The results were shown in FIG. 2, and clearly demonstrate the physical association of the natural lipids of the virus with the lipopeptides.

Figure 3:
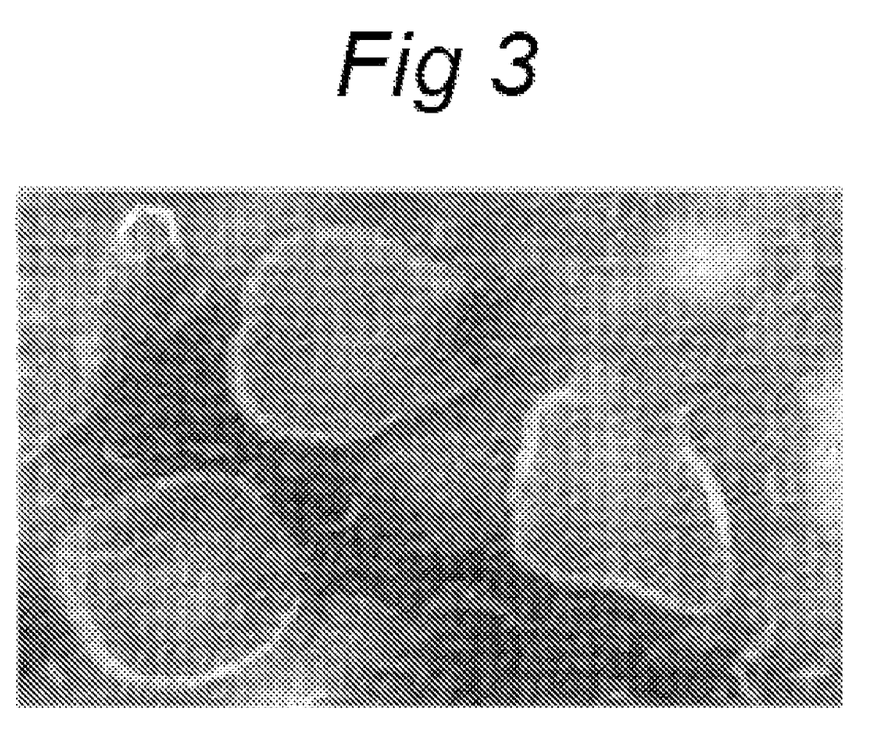
FIG. 3: Electron micrograph of reconstituted viral membranes containing lipopeptides according to the present invention; negative stain using ammonium phosphomolybdate. The membranes are about 100-200 nm in diameter.

Electron micrographs of the virosomes collected from the band of the gradient are shown in FIG. 3 and clearly show particles the size of viruses, displaying the viral antigen spikes that are characteristic of influenza viruses.

Example 2

Figure 4A:
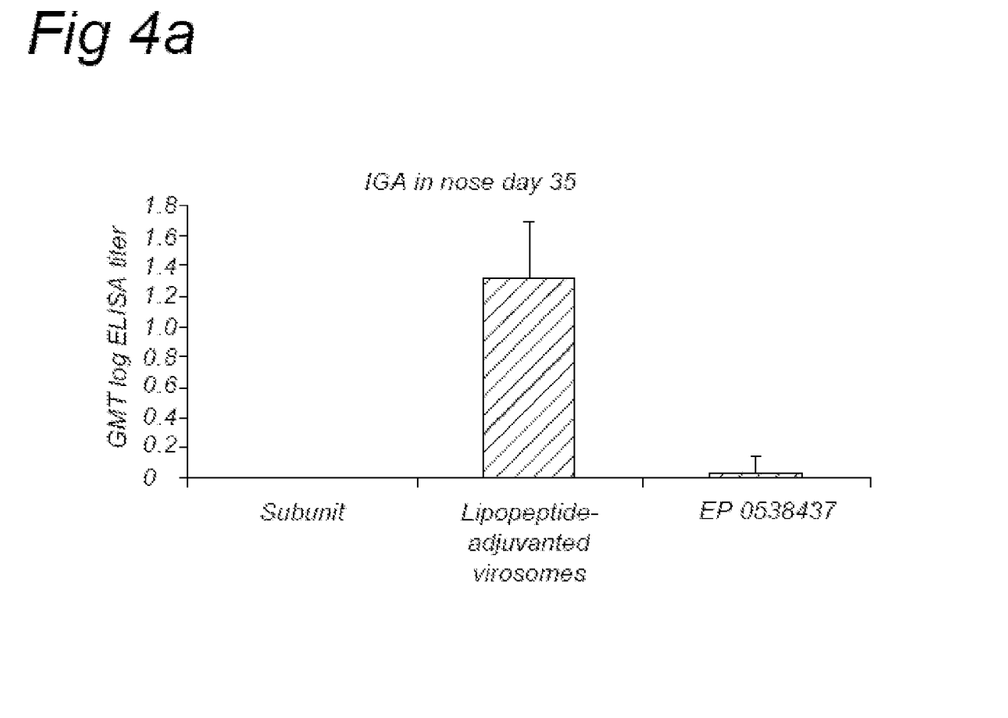
FIG. 4: IgA titers in nose and lung after two intranasal vaccinations with A/Panama/2007/99, 14 days apart; the titers were determined 3 weeks after the last vaccination. Pre-immune titers were subtracted. Vaccines used were a standard commercial subunit vaccine, virosomes prepared according to EP 0538437, or reconstituted viral membranes, containing lipopeptides, according to the present invention. Group size is 10 mice.
Figure 4B:
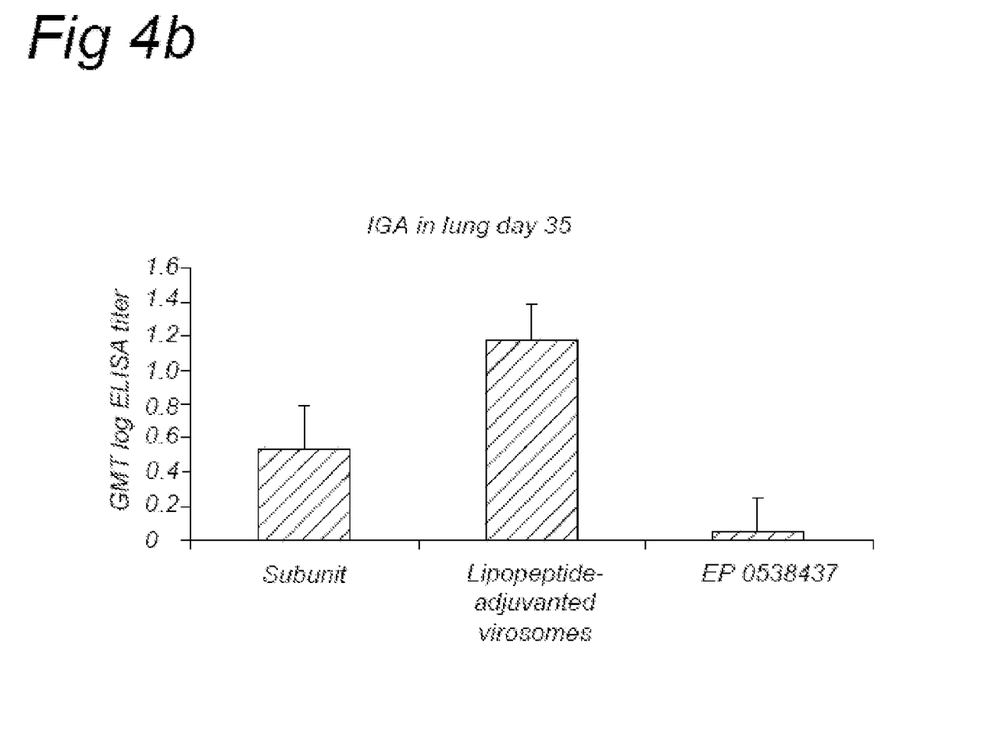
Figure 5:
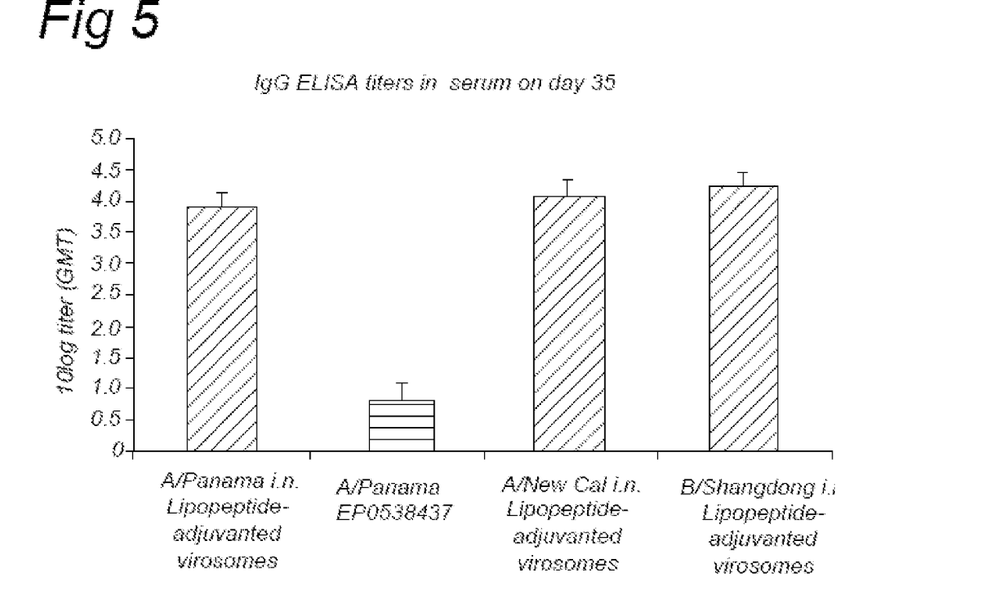
FIG. 5: IgG titers in blood after two intranasal vaccinations, 14 days apart; the titers were determined 3 weeks after the last vaccination. Pre-immune titers were subtracted. Vaccines used were virosomes prepared according to EP 0538437, or reconstituted viral membranes, containing lipopeptides, according to the present invention. Four different vaccine preparations, each containing antigen from one strain of virus as indicated, were used to vaccinate 4 groups of 10 mice.

Intranasal Immunization Experiments Using Reconstituted Viral Membranes Containing the Lipopeptide N-palmitoyl-S-2,3(bispalmitoyloxy)-propyl-cysteinyl-seryl-(lysil)₃-lysine, the Natural Lipids of Influenza Virus and the Influenza Membrane Proteins Vaccination by intranasal application of a reconstituted viral membrane containing the influenza virus hemagglutinin and N-palmitoyl-S-2,3(bispalmitoyloxy)-propyl-cysteinyl-seryl-(lysil)₃-lysine, was compared to intranasal application of a standard subunit vaccine, or a virosome vaccine prepared according to EP 0538437. Balb/C mice were immunized by a intranasal instillation of 10 microliters of antigen containing 5 μg of influenza proteins, on days 0, and 14. Blood samples were taken on day 0, 14, and 35, nasal and lung washes were collected on day 35. Several different strains of influenza virus were compared; mice were immunized with one type of strain each. Lung washes were performed by injection of 1.5 ml of PBS into the lungs via a syringe connected to the trachea, followed by aspiration of 1 mL of fluid. Nasal washes were collected by injecting 0.5 ml of PBS retrograde, via the trachea, into the nasopharynx, the lavage fluid being collected at the nostrils. Debris and cellular components were immediately removed from the lavage fluids by centrifugation, and a protease inhibitor mix (chemstatin, antipain, leupeptine, pepstatin, final concentration 1 microgram/ml, from a 1000× concentrated stock solution in dry DMSO) was added, after which the samples were frozen in liquid nitrogen and stored at −20 deg C. until analysis. Samples were analyzed by IgA in nose and lung and IgG ELISA against influenza proteins. The results are shown in FIG. 4 and FIG. 5 respectively.

Example 3

Membrane Fusion Activity of a Reconstituted Viral Membrane Containing the Lipopeptide N-palmitoyl-S-2,3(bispalmitoyloxy)-propyl-cysteinyl-seryl-(lysil)₃-lysine, the Natural Lipids of Influenza Virus, Pyrene-labeled Phosphatidylcholine, and the Influenza Membrane Proteins Purified and concentrated influenza A/Panama/2007/9 virus (1500 nmol phospholipid) was incubated with 1 ml of octa(ethylene glycol)-n-dodecyl monoether (C12E8) at a concentration of 100 mM, for 10 min at 4° C., in an isotonic buffer at neutral pH: 145 mM NaCl, 2.5 mM HEPES, 1 mm EDTA, pH 7.4 (Buffer A). The viral nucleocapsid and matrix protein were then removed by centrifugation at 100,000×g for 30 min at 4° C. The pellet was discarded. The supernatant was mixed with the dry lipopeptide and pyrene-labeled phospholipid at a ratio of 0.5 mg lipopeptide and 150 nmol 1-hexadecanoyl-2-(1-pyrenedecanoyl)-sn-glycero-3-phosphatidylcholine per 750 nmol of viral lipid, and mixed until the lipopeptide and pyrene-labeled phospholipid were dissolved. 128 mg of BioBeads SM-2 (Bio-Rad) were then added to each 350 microliters of the mixture, and the detergent was removed by shaking the mixture and the beads vigorously for one hour. The fluid was then transferred to another 64 mg of these beads and shaking was continued for 10 minutes.

Figure 6:
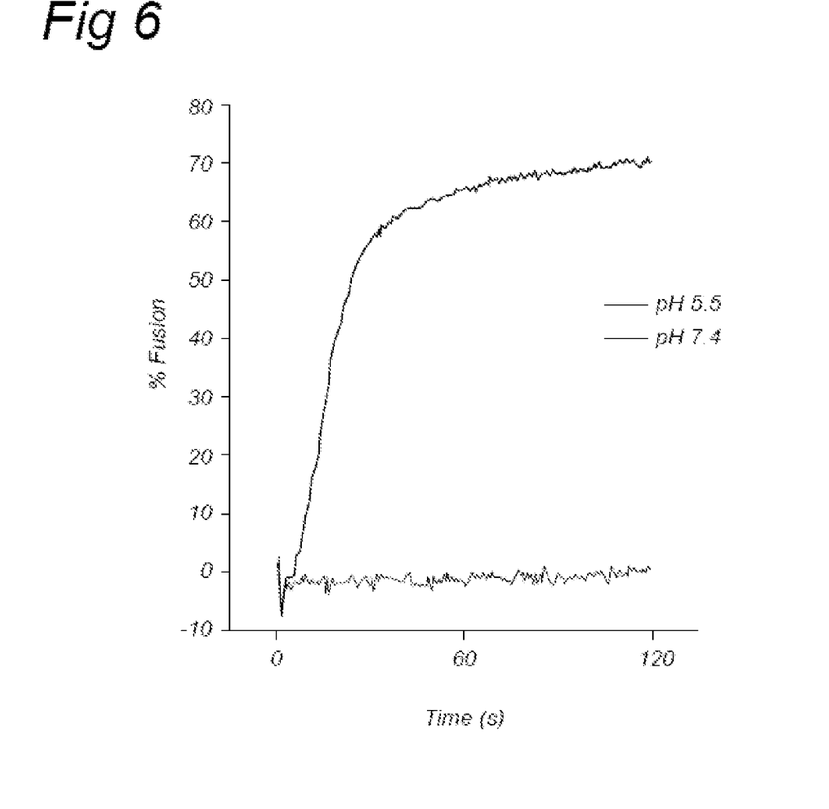
FIG. 6: Fusion activity of the reconstituted viral membranes according to the invention. Reconstituted viral membranes containing pyrene-phospholipid were mixed with erythrocyte ghosts and fusion was measured according the text.

For the measurement of membrane fusion, erythrocyte ghost target membranes were prepared from outdated red blood cell concentrates (blood type B, rhesus factor negative) by the method of Steck and Kant (1974) Fusion was measured at a concentration of 0.06 M of ghosts phospholipid and 1 μM of virosomal phospholipid, in a buffer containing 140 mM NaCl, 15 mM sodium citrate at pH 5.1. Lipid mixing was monitored by dilution of pyrPC. For this purpose, pyrene excimer fluorescence was measured, at excitation and emission wavelengths of 345 nm (bandpass 2 nm) and 490 nm (bandpass 16 nm), respectively, in the presence of a 475 nm cut-off filter in the emission beam. Background fluorescence was assessed at infinite dilution of the probe, which was obtained by adding 35 μl of 0.2 M C12E8. The changes in fluorescence were converted to extents of fusion (f) by calculating $f=100\times(E_0-E)/(E_0-E_y)$, where E represents excimer fluorescence at any time, and $E_0$ and $E_y$ represent, respectively, the intensities at 490 nm at time zero and after the addition of C12E8, both corrected for dilution effects. The results, shown in FIG. 6 clearly indicate strong fusion activity of the reconstituted membrane.

Example 4

Intramuscular Immunization Experiments Using Reconstituted Viral Membranes Containing the Lipopeptide N-palmitoyl-S-2,3(bispalmitoyloxy)-propyl-cysteinyl-seryl-(lysil)$_3$-lysine, the Natural Lipids of Influenza Virus and the Influenza Membrane Proteins, Compared to Immunization with Virosomes Prepared According to EP 0538437

Figure 7:
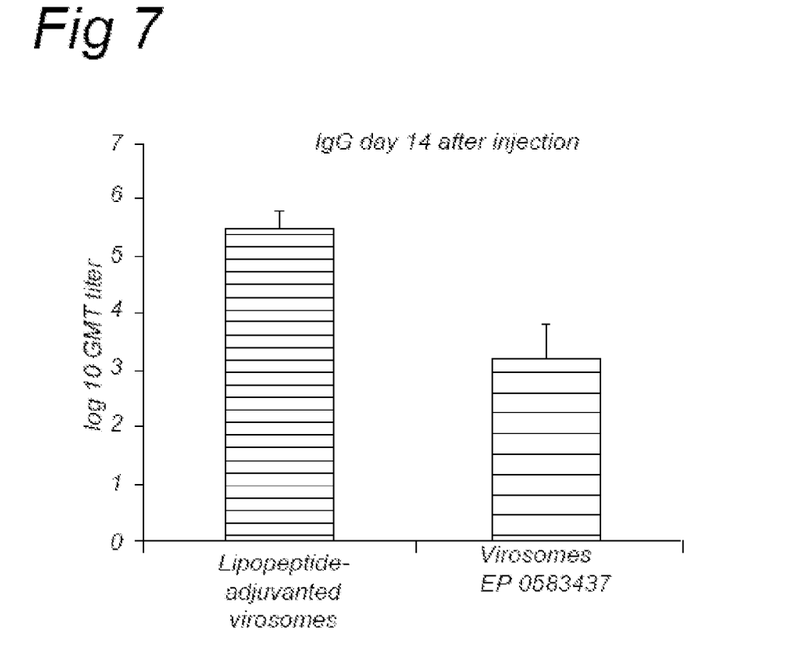
FIG. 7: IgG titers in blood after a single intramuscular vaccination; the titers were determined 3 weeks after vaccination. Pre-immune titers were subtracted. Vaccines used were virosomes prepared according to EP 0538437, or reconstituted viral membranes, containing lipopeptides, according to the present invention. Group size was 10 mice.
Figure 8:
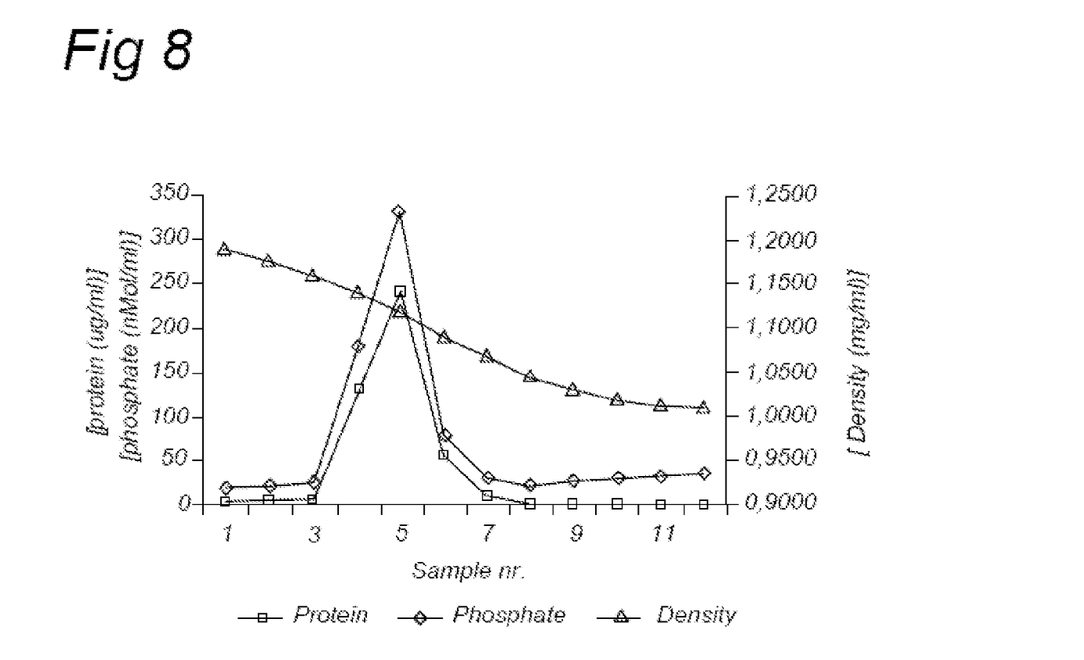
FIG. 8: Equilibrium density sucrose gradient analysis of reconstituted viral membranes from the A/Wyoming strain of virus, showing a single denisty peak of reconstituted material; lipopeptides were recovered from fractions 4, 5 and 6.
Figure 9:
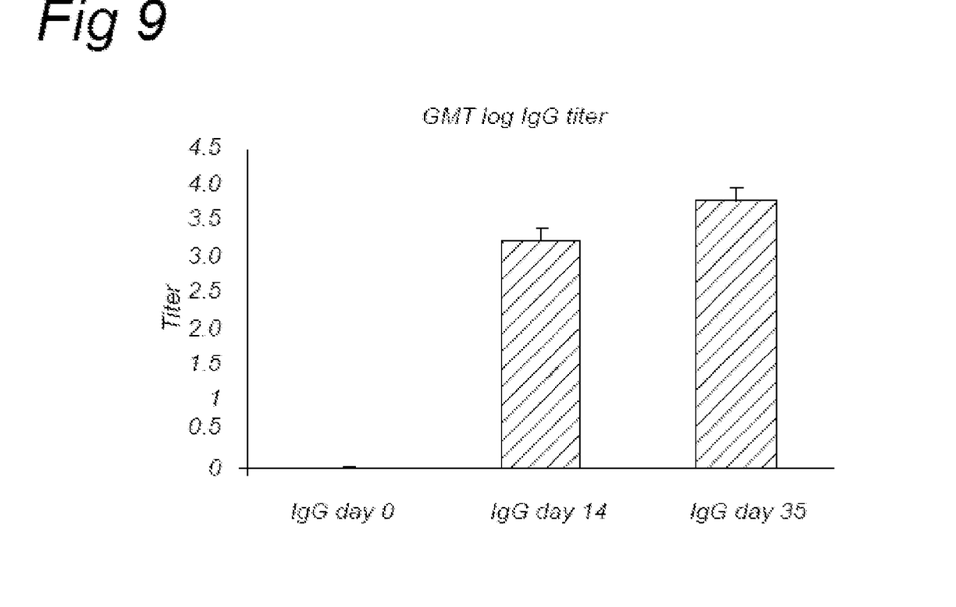
FIG. 9: IgG titers in blood after intranasal vaccinations on day 0 and 14, in a group of 10 mice. Antigen was from the A/Panama/2007/99 strain of virus, the membranes contained N-palmitoyl-S-2,3(bispalmitoyloxy)-propyl-cysteinyl-seryl-(prolyl)$_3$-proline.
Figure 10:
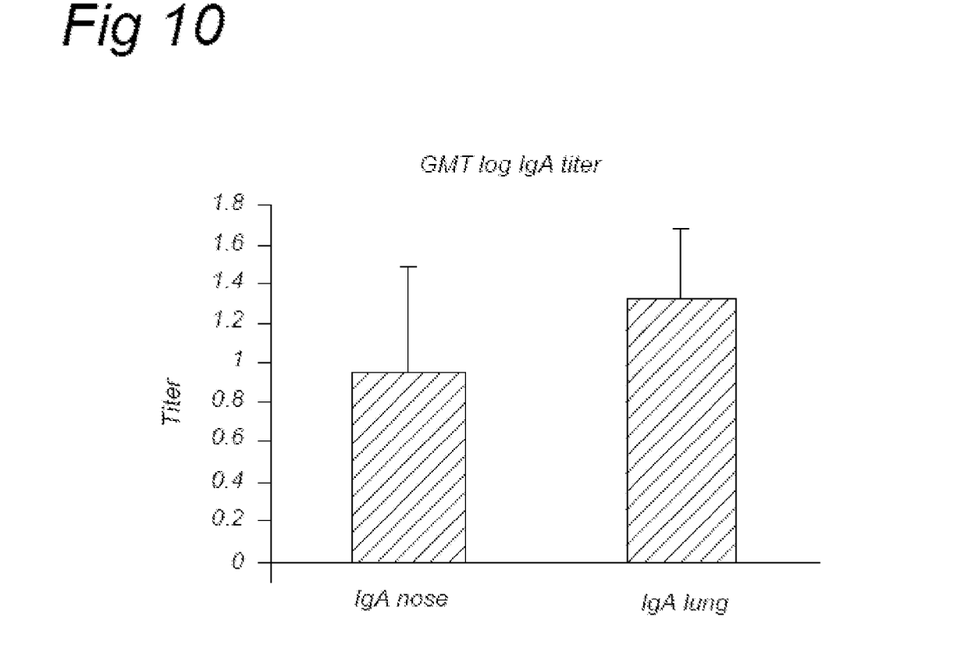
FIG. 10: IgA titers in nose and lung, in a group of 10 mice, after two intranasal vaccinations with reconstituted membranes of the A/Panama/2007/99 strain, containing the lipopeptide N-palmitoyl-S-2,3(bispalmitoyloxy)-propyl-cysteinyl-seryl-(prolyl)$_3$-proline, 14 days apart; the titers were determined 3 weeks after the last vaccination. Pre-immune titers were subtracted.

25 µl of influenza antigen (5 µg of protein) was injected in the muscle of one hind leg of Balb/C mice on day 0. Blood samples were taken on day 0 and 14. The A/Panama/2007/99 strain of virus was used for vaccine preparation. Samples were analyzed by IgG ELISA against influenza hemagglutinin. The results are shown in FIG. 7.

Example 5

Physical Characterization of Functionally Reconstituted Viral Membranes Containing the A/Wyoming Membrane Proteins by Equilibrium Density Gradient Centrifugation Reconstituted membranes viral membranes containing the lipopeptide N-palmitoyl-S-2,3(bispalmitoyloxy)-propyl-cysteinyl-seryl-(lysil)$_3$-lysine were prepared as described in example 1, loaded atop a 10-60% w/v sucrose gradient, en centrifuged at 50 000 rpm in a Beckman SW55 rotor for 16 hours. In this type of gradient, lipids and lipopeptides remain at the top, while proteins migrate to the bottommost fraction. Samples from the gradient were analyzed by refractometry, protein and phospholipid determination. The results, shown in FIG. 8 show that essentially all the viral protein and most of the viral lipid co-purify in a single peak. Also, lipopeptides were only recovered from fractions 4, 5 and 6. These data indicate that the reconstituted membranes are particles with a density of around 1.12 g/ml.

Example 6

Intranasal Immunization Experiments Using Reconstituted Viral Membranes Containing the Lipopeptide N-palmitoyl-S-2,3(bispalmitoyloxy)-propyl-cysteinyl-seryl-(prolyl)$_3$-proline, the Natural Lipids of Influenza Virus and the Influenza Membrane Proteins Membranes were prepared from A/Panama/2007/99 as described in example 1 above, and used to immunize mice as described in example 2. The ELISA IgG titers in serum, and the IgA titers in nose and lung are shown in FIGS. 9 and 10 respectively. These data indicate that the lysine and proline derivatives of N-palmitoyl-S-2,3(bispalmitoyloxy)-propyl-cysteinyl-seryl-result in approximately equivalent enhancement of the immune response.

TABLE 1

| Lipopeptides particularly suitable for making reconstituted viral membranes according to the invention. |
|---|
| N-palmitoyl-S-2,3(bispalmitoyloxy)-propyl-cysteinyl-seryl-serine |
| S-2,3(bispalmitoyloxy)-propyl-cysteinyl-seryl-serine |
| N-palmitoyl-S-2,3(bispalmitoyloxy)-propyl-cysteinyl-seryl-(lysil)$_3$-lysine |
| S-2,3(bispalmitoyloxy)-propyl-cysteinyl-seryl-(lysil)$_3$-lysine |
| N-palmitoyl-S-2,3(bisoleoyloxy)-propyl-cysteinyl-seryl(lysil)$_3$-lysine |
| S-2,3(bisoleoyloxy)-propyl-cysteinyl-seryl-(lysil)$_3$-lysine |
| N-palmitoyl-S-2,3(bismyristoyloxy)-propyl-cysteinyl-seryl-(lysil)$_3$-lysine |
| S-2,3(bismyristoyloxy)-propyl-cysteinyl-seryl-(lysil)$_3$-lysine |
| N-palmitoyl-S-3(palmitoyloxy)-propyl-cysteinyl-seryl-(lysil)$_3$-lysine |
| N-palmitoyl-S-2,3 hydroxy-propyl-cysteinyl-seryl-(lysil)$_3$-lysine |
| N-palmitoyl-S-2,3(bispalmitoyloxy)-propyl-cysteinyl-seryl-(prolyl)$_3$-proline |
| N-palmitoyl-S-2,3(bispalmitoyloxy)-propyl-cysteinyl-seryl-(glutaminyl)$_3$-glutaminic acid |

REFERENCES

Arkema, A. (2000) Vaccine 18: 1327-1333

Böttcher C. J. F, Van Gent C. M., Fries C. J. (1961) Anal Chim Acta 24:203-204

Bungener, L (2002) Vaccine 20: 323-338

Cox J. C., Sjolander A., Barr I. G. (1998) Adv Drug Delivery 32: 247-271

Dinarello, C. A. (1978) J. Infect. Dis. 138: 760-767

Folch, H. et al. (1957) J. Biol. Chem 226, 497-509

Glück, R. et al., (1994) J Infect Dis 181: 1129-1132

Hernandez, L. D: et al., (1996) Ann. Rev. Cell Dev. Biol. 12:627-661

Janeway, C. et al. (2001) Immunobiology, 5th edition, Garland Publishing, New York Kohashi, O. et al. (1980) Infect. Immun. 20: 70-75

Kotani, S. et al., (1976) Biken J. 19: 9-13

Morein et al. (1984) Nature 308: 457-460

Ogra P L, Faden H, Welliver R C (2001) Clin Microbiol Rev 14: 430-445

Powell, M. F. et al., (1988)5: 528-532

Ribi, E. E. (1979) Cancer Res. 39:4756-4759

Steck, T. L. and Kant, J. A. (1974) Meth. Enzym. 31: 172-180

Stegmann T., Morselt H. W. M., Booy F. P., Van Breemen J. F. L., Scherphof G., Wilschut J. (1987) EMBO J 6: 2651-2659

Weijzen S, et al., (2002) J Immunol 169:4237-4238

The invention claimed is:

1. A reconstituted viral membrane, the lipid bilayer of which comprises a fusion protein of a virus, an amphiphilic adjuvant and, optionally, a further antigen, whereby:

(a) the lipid bilayer has a lipid composition that is compatible with fusion, induced by the fusion protein, of the viral membrane with the membrane of a cell that can be fused with the virus from which the fusion protein is derived;

(b) the fusion protein and the amphiphilic adjuvant are incorporated within the hydrophobic interior of the lipid bilayer; and, (c) the fusion protein, the amphiphilic adjuvant and the optional further antigen are not covalently linked; and wherein the amphiphilic adjuvant is a lipopeptide.

2. A reconstituted viral membrane according to claim 1, wherein the lipid bilayer comprises natural lipids of a viral membrane.

3. A reconstituted viral membrane according to claim 1, wherein the amphiphilic adjuvant is a ligand for a mammalian Toll-like receptor.

4. A reconstituted viral membrane according to claim 1, wherein the lipopeptide is selected from the group consisting of: N-palmitoyl-S-2,3(bispalmitoyloxy)-propyl-cysteinyl-seryl-serine, S-2,3(bispalmitoyloxy)-propyl-cysteinyl-seryl-serine, N-palmitoyl-S-2,3(bispalmitoyloxy)-propyl-cysteinyl-seryl-(lysil)$_3$-lysine, S-2,3(bispalmitoyloxy)-propyl-cysteinyl-seryl-(lysil)$_3$-lysine, N-palmitoyl-S-2,3(bisoleoyloxy)-propyl-cysteinyl-seryl-(lysil)3-lysine, S-2,3(bisoleoyloxy)-propyl-cysteinyl-seryl-serine-(lysil)$_3$ -lysine, N-palmitoyl-S-2,3(bismyristoyloxy)-propyl-cysteinyl-seryl-(lysil)$_3$-lysine, S-2,3(bismyristoyloxy)-propyl-cysteinyl-seryl-(lysil)$_3$-lysine, N-palmitoyl-S-3 (palmitoyloxy)-propyl-cysteinyl-seryl-(lysil)$_3$-lysine and N-palmitoyl-S-2, 3hydroxyl-propyl-cysteinyl-seryl-(lysil)$_3$lysine, N-palmitoyl-S-2,3(bispalmitoyloxy)-propyl-cysteinyl-seryl-(prolyl)$_3$-proline, N-palmitoyl-S-2,3(bispalmitoyloxy)-propyl-cysteinyl-seryl-(glutaminyl)$_3$-glutaminic acid.

5. A reconstituted viral membrane according to claim 1, wherein at least one of a fusion protein of a virus or a further antigen is an integral membrane protein.

6. A reconstituted viral membrane according to claim 1, wherein at least one of a fusion protein of a virus or a further antigen is a viral antigen.

7. A reconstituted viral membrane according to claim 6, wherein at least one of a fusion protein of a virus or a further antigen is from an influenza virus.

8. A reconstituted viral membrane according to claim 7, wherein at least one of a fusion protein of a virus or a further antigen is a hemagglutinin (HA), a neuraminidase (NA) or an M2 protein.

9. A reconstituted viral membrane according to claim 6, wherein at least one of a fusion protein of a virus or a further antigen is derived from a virus selected from the group consisting of Retroviridae, rubellavirus, Paramyxoviridae, Flaviviridae, Herpesviridae, Bunyaviridae, Arenaviridae, Hantaviridae, Coronaviridae, Papovaviridae, Rhabdoviridae, Coronaviridae, Alphaviridae, Arteriviridae, Filoviridae, Arenaviridae, poxviridae, and African swine fever virus.

10. A reconstituted viral membrane according to claim 1, wherein the further antigen is derived from a parasite, a bacterium, a fungus, a yeast, or wherein the further antigen is a tumor-specific antigen.

11. A pharmaceutical composition comprising a reconstituted viral membrane as defined in claim 1 and a pharmaceutically acceptable carrier.

12. A pharmaceutical composition according to claim 11, whereby the composition is suitable for intranasal, oral or parental administration.

13. A reconstituted viral membrane according to claim 2, wherein the amphiphilic adjuvant is a ligand for a mammalian Toll-like receptor.

14. A reconstituted viral membrane according to claim 2, wherein at least one of a fusion protein of a virus or a further antigen is an integral membrane protein.

15. A reconstituted viral membrane according to claim 3, wherein at least one of a fusion protein of a virus or a further antigen is an integral membrane protein.

16. A reconstituted viral membrane according to claim 4, wherein at least one of a fusion protein of a virus or a further antigen is a hemagglutinin (HA), a neuraminidase (NA) or an M2 protein.

17. A reconstituted viral membrane according to claim 16, wherein the fusion protein of a virus is a hemagglutinin (HA) and the further antigen is a neuraminidase (NA).

* * * * *